United States Patent [19]

Barger et al.

[11] Patent Number: 4,636,767

[45] Date of Patent: Jan. 13, 1987

[54] MIXED SEMICONDUCTOR FILM DEVICE FOR MONITORING GASES

[75] Inventors: William R. Barger, Fort Washington; Neldon L. Jarvis, Joppa, both of Md.; Arthur W. Snow, Alexandria; Henry Wohltjen, Burke, both of Va.

[73] Assignee: The United States of America as represented by the Secretary of the Navy, Washington, D.C.

[21] Appl. No.: 768,004

[22] Filed: Aug. 21, 1985

[51] Int. Cl.⁴ .................. G01N 27/04; H01C 13/00
[52] U.S. Cl. ................................. 338/34; 338/309; 324/71.1; 324/71.5; 427/35; 427/82
[58] Field of Search ............... 427/82, 35; 338/309, 338/34; 324/62, 71.1, 71.5

[56] References Cited

U.S. PATENT DOCUMENTS

| 2,758,256 | 9/1952 | Eisler | 338/309 X |
| 3,056,935 | 10/1962 | Jensen | 338/34 X |
| 4,381,922 | 5/1983 | Frey et al. | 427/82 X |
| 4,539,061 | 9/1985 | Sagiv | 427/35 X |

Primary Examiner—A. C. Prescott
Attorney, Agent, or Firm—Robert F. Beers; Sol Sheinbein; Edward V. Hiskes

[57] ABSTRACT

A method of monitoring gases using electronic conductivity changes in ordered organic semiconductor films comprising an insulated substrate fabricated to an interdigital microelectrode and coated with a vapor sensitive semiconductor film. Variations in current flow caused by vapors interacting with the film are indicative of the vapor type.

7 Claims, 5 Drawing Figures

Table I. Maximum Per Cent Change in Conductance due to Vapor Exposures

| Central Atom (M) | Test Vapor and Concentration | | |
|---|---|---|---|
| | $NH_3$ 2 ug/L | DMMP 10 ug/L | $SO_2$ 20 ug/L |
| $H_2$ | 18 | 14 | 26 |
| Co | −1.3 | 0.5 | −4.3 |
| Ni | 185 | 128 | 13 |
| Pd | 63 | 27 | 15 |
| Pt | 163 | 69 | 40 |
| Cu | 137 | 16 | 0 |
| Zn | −8.1 | −2.2 | −2.6 |
| Pb | 0 | 0 | 0 |

Values are the average of 2 sequential exposures of the test vapor to 45-layer L-B films of M-Pc(Cp)$_4$ mixed with octadecanol on 5mm x 8mm electrodes.

FIG. 5

MIXED SEMICONDUCTOR FILM DEVICE FOR MONITORING GASES

BACKGROUND OF THE INVENTION

The present invention relates generally to chemiresistor and more specifically to phthalocyanine film chemiresistors. A chemiresistor is a device which exhibits the electrical characteristics of a resistor whose conductance is modulated by the presence or absence of some chemical species in contact with the device. Such devices have been sought for many years as very simple and sensitive chemical sensors for process control and environmental monitoring applications. It is well known that semiconductors exhibit characteristic electronic conductivities which are strongly affected by ambient chemical vapors. Indeed, much effort has been expended worldwide investigating heated metal oxide semiconductors such as tin oxide and zinc oxide as vapor sensors. In spite of extensive development of these devices, they have proven to be less than ideal since they do not detect vapors very selectively or at concentrations below a few parts per million, and they are not readily suited for integration into conventional monolithic silicon technology.

Organic semiconductor films containing phthalocyanine are an alternative to heated metal oxides. Devices employing sublimed or evaporated films have high sensitivity to vapors. However, these devices typically exhibit slow response to vapor concentration changes.

An improved semiconductor film may be produced for use in a chemiresistor using substituted phthalocyanines and the Langmuir-Blodgett film deposition technique. An example of this, using phthalocyanines with carbon substitutions on the phthalocyanine ring is seen in Baker et al., IEEE Proceedings, Vol. 130, Pt. 1, No. 5, October 1983.

However, the use of carbon-carbon bonds to attach substituents to the phthalocyanine ring is disadvantageous because the creation of such bonds involves expensive and difficult processing steps. Ether, or thioether, linked substituents allow for substantially more economical and reliable manufacturing processes.

SUMMARY OF THE INVENTION

Accordingly, one object of this invention is to produce a chemiresistor which can be readily integrated with monolithic integrated circuit technology.

Another object of this invention is to produce a chemiresistor which has improved sensitivity toward low concentrations of vapor.

Yet another object of this invention is to produce a chemiresistor which does not involve the use of carbon-substituted phthalocyanine compounds.

Yet another object of this invention is to produce chemiresistor films with improved order and transfer characteristics.

These and other objects are achieved by depositing ordered films of aryloxy, arylthio, alkyloxy, or alkylthio substituted phthalocyanines deposited on a non-conducting substrate between interdigital electrodes. Ether or thioether bonds link the substituent to the ring. Films with improved order and ease of deposition are made by using a mixture of substituted phthalocyanine with a second substance, such as stearyl alcohol.

BRIEF DESCRIPTION OF THE DRAWINGS

FIG. 5 contains tabular information on conductance change due to vapor exposure.

DETAILED DESCRIPTION OF THE INVENTION

Figure 1:
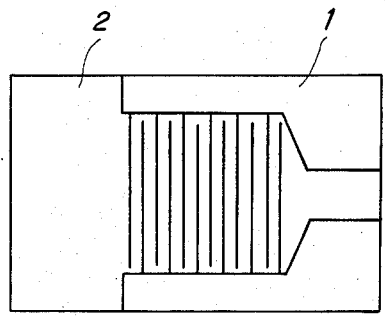
FIG. 1 is a diagram of an interdigital electrode chemiresistor.

An example of a device constructed in accordance with the teachings of this invention is shown in FIG. 1.

The device comprises a conductive member 1, a substrate member 2, and an ordered film overlying both 1 and 2.

The conductive member 1 may be any material which can be placed in contact with the overlying film, and which conducts electricity. The material is preferably a good conductor, and one which is inert with respect to the type of vapor to which the sensor will be exposed. Gold metal is a particularly desirable material. However, it is conceivable that the conductive member could be composed of any metal, including even a confined drop of mercury held against the film. Alternatively, the conductor could be an organic material or other substance.

The substrate member 2 must be an insulating material to which the overlying film may be applied. Silicon, such as that used in semiconductor wafers is a suitable material, as is quartz. Various non-conductive plastics or ceramics could also be used.

Figure 2:
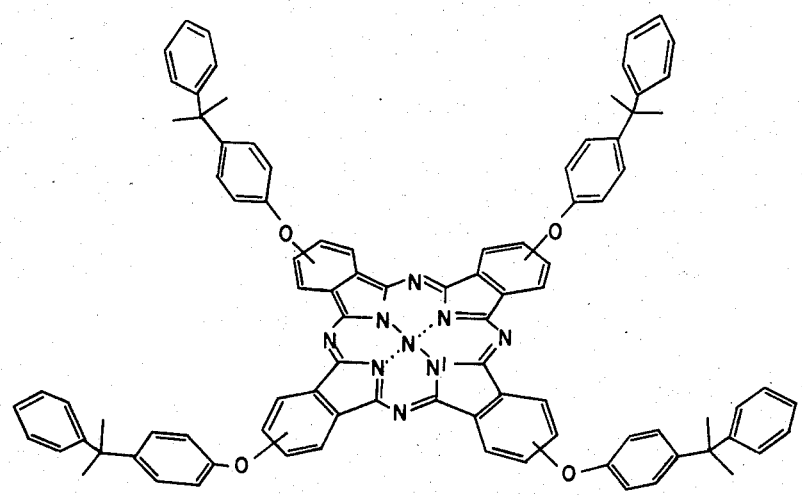
FIG. 2 is a diagram of the structure of substituted phthalocyanine.

The said film is deposited by the Langmuir-Blodgett technique, wherein the organic semiconductor is depostied as an ordered sheet, one molecular layer at a time. The organic semiconductors used for film forming in tested examples of this invention are metal-tetracumylphenoxy phthalocyanines, which are derivatives of metal-phthalocyanines. The structure of nickel tetracumylphenoxy phthalocyanine is shown in FIG. 2.

Figure 3:
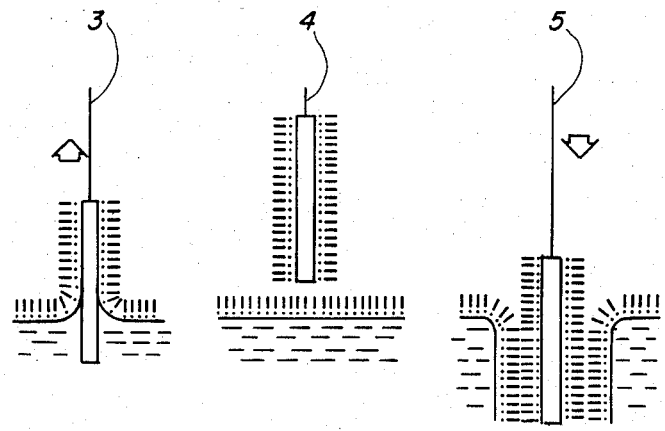
FIG. 3 is a series of three diagrams illustrating the Langmuir-Blodgett film transfer process onto substrate and electrodes of a chemiresistor.

In a preferred method of producing the said overlying film, the substituted phthalocyanine is first mixed with another substance that is known to form very good Langmuir-Blodgett (L-B) films. For example, it has been found that metal-tetracumylphenoxy phthalocyanines mixed with stearyl alcohol (octadecanol) will produce superior L-B films with excellent reproducibility. It was not obvious that such a mixed film could maintain its semiconducting and vapor sensitive cheacteristics when mixed with an inert material such as stearyl alcohol. However, experimental results indicate that such mixed L-B films retain, and even improve upon, the desirable semiconducting and vapor sensitive properties found in unmixed films deposited by other techniques. FIG. 3 contains three views illustrating steps in the L-B film forming process. In the first view, a rectangular bar of substrate material, with electrodes already affixed to the wide, flat surface of the bar, is drawn upward, from a state of being immersed in water, out into the open atmosphere. As the bar passes from the water to the air, a layer of film-forming molecules floating on the surface of the water attach themselves to the bar to form a monolayer covering over the bar. A bar with one monolayer of film-forming molecules is seen in the second view of FIG. 3. In the final view of FIG. 3, the bar is reimmersed into the water. In the course of this re-immersion, an additional layer of film is deposited. This process may be repeated to add additional layers. The three views of FIG. 3 are labeled as (3), (4), and (5).

It should be noted that unmixed films of these ether-linked substituted phthalocyanines contain substantial irregularities, and may not deposit in monolayer form. This degrades device performance. Thus, the use of mixed film is highly recommended. With mixed films, highly regular, monolayer films in excess of 100 layers thick have been produced.

Furthermore, it appears that best results are achieved if the substituent contains an aryl group. Alkyl substituents do not produce optimally uniform film transfer. Thus, the use of metal or hydrogen-containing tetracumulphenoxy phthalocyanine is recommended as the best mode for practicing this invention.

The ordered nature of the film produced by the L-B coating technique appears to be critical to proper chemiresistor operation. This is thought to be so because heating to the film melting point causes an irreversible loss of film conductivity. It appears that the loss of conductivity results when melting causes the order of the film to be disrupted. When this order disappears, the film acts as one would expect a film containing a large amount of stearyl alcohol to act, that is, as a non-conductor.

Examples

Several chemiresistors have been fabricated using a quartz substrate upon which two interdigital electrodes of gold have been deposited. The device layout, showing gold electrodes 1, and quartz substrate 2, is seen in FIG. 1. In the tested devices, the electrodes have 40 finger pairs with an overlap distance of 3200 microns. Each finger is 20 microns wide, and there is a 20 micron gap between fingers. Although the entire 5 mm×8 mm electrode is coated with organic film, the active area is 3.2 mm×3.2 mm. To deposit the L-B films on the electrodes, the entire quartz wafer and electrode assembly is repeatedly dipped in an L-B film forming solution.

The L-B film forming solution is composed as follows: known solutions of stearyl alcohol in chloroform and metal-phthalocyanine in chloroform are mixed. These are mixed in such proportions as to achieve the desired ratio of stearyl alcohol and phthalocyanine in the final film. A 1:1 mole ratio works well. Then the mixture is spread upon a water surface. The chloroform evaporates, leaving a monolayer on the surface of the water. The film pressure is regulated by either contracting or expanding the water surface area available upon which the film may float. This may be accomplished by confining the floating film on one side with a movable parrafin bar. For manufacture of the test devices, the pressure was maintained at 20 mN per meter. However, the person skilled in the art of L-B film deposition will recognize that other pressures will also work.

The quartz substrate is dipped into the film on water repeatedly until the desired number of monolayers has been deposited. The tested devices were passed through the film-water interface a total of 45 times, to produce a total of 45 monolayers.

The metal atoms used in the tested examples of tetracumylphenoxy phthalocyanine films included Co, Ni, Pd, Pt, Cu, Zn, and Pb. One device was fabricated with hydrogen used in place of metal.

To determine I-V curves, the chemiresistors were mounted in flowing streams of dry air and the D.C. voltage was stepped by small increments through the range of $-1$ to $+1$ volts. The newly fabricated devices gave linear I-V curves in this range after 3 or 4 runs. Initial irregularities may be due to the incorporation of vapor water or absorption of atmospheric gasses into the coating during fabrication. These vapors may leave the chemiresistor as the dry air is passed over.

The linear I-V curves corresponded to resistances in the range of 10 E-10 to 10 E-11 for all of the 45 layer devices. Other tests indicated that device conductivity increases as a linear function of the number of layers present. It was also found that device conductivity increases with temperature. Accordingly, the device conductivity increases with temperature. Accordingly, the devices were placed in a stainless steel cell and held at 33° C. for testing purposes.

Conductivity changes of eight devices with different coatings have been measured under conditions of exposure to a series of vapors. A gas exposure apparatus with permeation tubes was used to test the chemiresistors with 45 layer L-B film coatings against exposures to the following vapors; 2 micrograms/1 ammonia; 10 micrograms/1 dimethyl methyl phosphonate (DMMP); and 20 micrograms/1 of sulfur dioxide. For 100 seconds, an atmosphere with these vapor concentrations flowed over a chemiresistor in place of a carrier steam of dry air, and the change in conductivity was recorded. The data for an exposure to ammonia of a device coated with the nickel tetracymylphenoxy phthalocyanine/-stearyl alcohol is given in FIG. 4. Arrows 6 indicate when the ammonia was switched in, and arrows 7 indicated when it was switched out.

Figure 4:
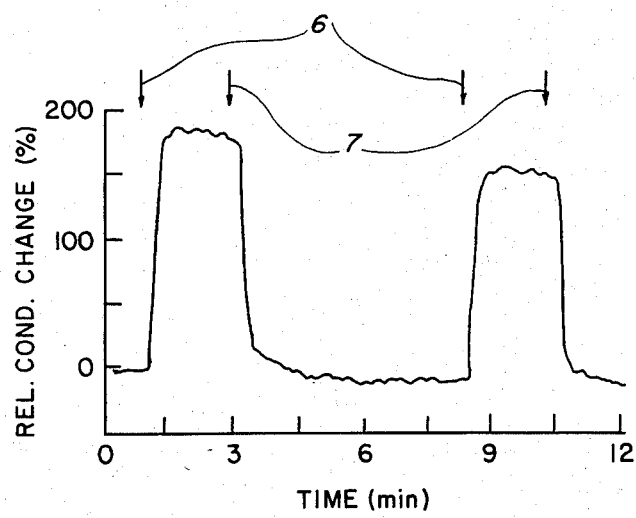
FIG. 4 is a graph demonstrating the conductivity change that occurs in one example chemiresistor of this invention, under actual operating conditions.

Notable features of the data in FIG. 4 are the rapid response and reversibility of the sensor. Rapid reversibility suggests that strong bonds are not formed between the coating and the vapor. Rapid response is thought to be due to the thinness of the coating film.

The maximum responses during the 100 second exposure for the entire series studied are listed in FIG. 5. One interesting feature of the data in FIG. 5 is that the films which give the greatest response to the test vapors all contain metals with either the dB (Ni, Pd, Pt) or d9 (Cu) electron configurations.

Since, as FIG. 5 demonstrates, the sensitivity and selectivity of the chemiresistor depends upon the metal in the phthalocyanine, arrays of chemiresistors with different metals therein can give recognizable response patterns for individual vapors. Both qualitative and quantitative information is obtained.

It is reasonable to believe that thioether linkages could be used in place of ether linkages in this invention.

Various substituted phthalocyanine compounds that may be used to build chemiresistors within the scope of this invention may be synthesized as follows:

EXAMPLES

Precursor Synthesis 4-(Cumpylphenoxy)-4-phthalonitrile (I). (I) was prepared by $K_2CO_3$-catalyzed nitro displacement of 4-nitrophthalonitrlile (Eastman) by cumylphenol (Aldrich) in $Me_2SO$. In a nitrogen atmosphere, 19.56 g (0.141 mol) of finely grounded anhydrous $K_2CO_3$ was added to a solution of 19.08 g (0.090 mol) of 4-cumylphenol and 15.57 g (0.090 mol) of 4-nitrophthalonitrile in 150 mL of dry Me$_2$SO by 1-2-g additions at $\frac{1}{2}$ to 1-h intervals over an 8-h period. The mixture was stirred for 24 hours at 20° C. under nitrogen. The reaction was methylene chloride and combined with two subsequent 50-ml extractions. The methyene worked up by filtering the undissolved salt and slowly adding the filtrate to a rapidly stirred 400-mL volume of water. The suspension was neutralized with HCl, and the crude products were taken up into 100 mL of chloride and combined with two subsequent 50-ml extractions. The methyene chloride solution was then extracted with 100 ml of 5% Na$_2$CO$_3$ to remove unreacted phenol, washed, and dried and solvent stripped to yield 21.3 g (70%) of I. The crude product was recrystallized twice from methanol yielding large platelets; MP 90° C.; IR (KBr) 3082 w, 3059 w, 3038 w, 2976 m, 2956 w, 2872 w, 2238 m, 1531 s, 1563 m, 1502 s, 1487 s, 1313 s, 1303 s, 1288 s, 1278 s, 1255 s, 1210 s, 1176 m, 1018 m, 901 m, 861 s, 769 m, 704 cm$^{-1}$; H NMR (CDCl$_3$) 1.70 (s, 6H, methyl), 7.72 (m, 12 H, aromatic); mass spectrum, m/e 338 (calcd 338). Anal. Calcd for C$_{23}$H$_{18}$N$_2$O: C, 81.65; H, 5.32; N, 8.23. Found: C, 81.86; H, 5.28; N, 8.23. On standing for several weeks the platelet crystal turn light green which is associated with the presence of a trace quantity of occluded methanol. Recrystallization from hexane proceeds yields needle-shaped crystals, mp 90° C., which remain colorless indefinitely. Anal. Found: C, 81.72; H, 5.41; N, 8.33.

4-(Cumypphenoxy)-4-phthalonitrile is hereafter referred to as reagent (I).

PHTHALOCYANINE SYNTHESES

With the exception of the metal-free derivative, the procedures for the metallophthalocyanines are very similar and analogous to those reported by Linstead and co-workers for unsubstituted metallophthalocyanines. Since the solubility properties of the phthalocyanine products are determined by the cumylphenoxy groups, the workup and purification procedures are also very similar. The general reaction and purification procedures are as follows except where departures are specified.

To a 10×75 mm tube fitted with an 8-mm Teflon-coated magnetic stirring bar were added the prescribed quantities of I and coreactant. The mixture was carefully fused under vacuum (less than 0.1 torr) to remove residual methanol occluded in I and sealed under vacuum. The entire tube was heated with stirring for the designated time and temperature. The crude product was purfied by column chromatography (neutral Woelm, activity 1) using toluene as a loading solvent and dioxane as an elution solvent. The dioxane solution was concentrated to a 2-3-mL volume, and the phthalocyanine was precipitated by dropwise addition into a stirred volume of 200 mL of methanol. The flocculent blue precipiate was filtered into the thimble of a micro Soxhlet extractor, extracted with methanol to ensure complete removal of unreached I, and extracted into benzene. The benzene solution was concentrated to a 3-mL volume and added dropwise to 200 mL of stirred petroleum ether. The flocculent product was collected and vacuum dried (180° C./0.1 torr).

METAL-FREE TETRAKIS (CUMYLPHENOXY) PHTHALOCYANINE (II)

A mixture of 1.00 g(2.96 mmol) of I and 0.081 g (0.74 mmol) of hydroquinone (purified by sublimation) was fused by gentle heating to the melting point without vacuum, cooled, sealed under vacuum, and reacted at 180° C. for 16 h: yield 0.49 g(49%); UV-vis (dioxane) 286, 341, 390, 602, 635, 663, 697 nm; IR (supported film on NaCl) 3290 w (N-H), 3093 w, 3062 w, 3040 w, 2977 m, 2940 w, 2877 w, 1607 m, 1508 s, 1477 s, 1237 s, 1176 m, 1093 m, 1017 s (H$_2$Pc specific band), 932 m, 830 m, 766 m, 747 s, 701 s cm$^{-1}$; H NMR (CDCl$_3$) 6.4 (br s, 2 H, internal N-H), 1.73 (s, 12 H, methyl), 7.32 (m, 24 H, aromatic); mass spectrum m/e 1355 (P+1). Anal. Calcd for C$_{92}$H$_{74}$N$_8$O$_4$: C, 81.51; H, 5.50; N, 8.27. Found: C, 81.61; H, 5.62; N, 8.43.

TETRAKIS (CUMYLPHENOXY) PHTHALOCANINE COPPER (III)

A mixture of 0.676 g (2.00 mmol) of I and 0.245 g (4.00 mmol) of copper bronze (Creslite) was reacted at 270° C. for 12 h: yield 0.302 g (43%); UV-vis (dioxane) 280, 347, 606, 674, nm; IR (supported film on NaCl) 3097 w, 3063 w, 3042 w, 2988 m, 2943 w, 2879 w, 1607 s, 1508 s, 1408 m, 1447 m, 1242 s, 1182 m, 1126 m, 1100 m, 969 m, 832 m, 768 m, 752 s, 704 s cm$^{-1}$; H NMR (CDCl$_3$) 1.65 (br s, 12 H, methyl), 7.25 (br s, 24 H, aromatic); ESR (1:10 CuPcX$_4$ H$_2$ PcX$_4$, toluene) g=2.34, 2.21, 2.04 (hfs), 1.96 (hfs) mass spectrum m/e 1416 (P+1).

Anal. Calcd for c$_{92}$H$_{72}$N$_8$O$_4$Cu: C, 78.00; H, 5.12; N, 7.91; Cu, 4.48. Found: C, 78.19; H, 50.01; N, 7.99; Cu 4.61.

TETRAKIS (CUMYLPHENOXY) PHTHALOCYANINE NICKEL (IV)

A mixture of 0.676 g (2.00 mmol) of I and 0.245 g (4.00 mmol) of nickel powder (HCl etched, washed, and dried) was reacted at 280° C. for 44 h: yield 0.534 g (76%); UV-vis (dioxane) 290, 340, 600, 667 nm: IR (supported film on NaCl) 3096 w, 3063 w, 3039 w, 2978 m, 2940 w, 2878 w, 1608 s, 1508 s, 1477 s, 1417 m, 1242 s, 1181 m, 1127 m, 1099 m, 1021 m, 963 m, 830 m, 768 m, 756 s, 703 s cm$^{-1}$; ESR (toluene) g=2 (s, Hpp=6 G); mass spectrum, m/e 1411 (P+1).

Anal. Calcd for C$_{92}$H$_{72}$N$_8$O$_4$Ni: C, 78.23; H, 5.14; N, 7.93; Ni, 4.16. Found: C, 78.00; H, 5.23; N, 7.82; Ni, 3.96.

TETRAKIS (CUMYLPHENOXY) PHTHALOCYANINE PALLADIUM (V)

A mixture of 0.676 g (2.00 mmol) of I and 0.088 g (0.50 mmol) of PdCl$_2$ (Alfa) was reacted at 290° C. for 48 h: yield 0.109 g (15%); UV-vis (dioxane) 283, 329, 612, 660 nm; IR (supported film on NaCl) 3093 w, 3064 w, 3038 w, 2977 m, 2938 w, 2880 w, 1608 s, 1508 s, 1455 s, 1409 m, 1242 s, 1172 m, 1131 m, 1110 m, 832 s, 767 m, 751 m, 702 s cm$^{-1}$; ESR (toluene) g=2 (s, Hpp=8 G).

Anal. Calcd for C$_{92}$H$_{72}$N$_8$O$_4$Pd: C, 75.68; H, 4.97; N, 7.76; Pd, 7.29. Found: C, 75.94; H, 4.99; N, 7.35; Pd, 7.25.

TETRAKIS (CUMYLPHONOXY) PHTHALOCYANINE PLATINUM (VI)

A mixture of 1.00 g (2.96 mmol) of I and 0.20 g (0.75 mmol) of PtCl$_2$ (Alfa) was reacted at 290° C. for 48 h: yield 0.263 g (23%); UV-vis (dioxane) 278, 394, 605, 651 nm; IR (supported film on NaCl) 3096 w, 3063 w, 3040 w, 2978 m, 2940 w, 2878 w, 1608 s, 1508 s, 1475 s, 1411 m, 1242 s, 1174 m, 1136 m, 1111 m, 831 m, 768 m, 753 m, 702 s cm$^{-1}$; ESR (toluene) g=2 (s, Hpp=4 G).

Anal. Calcd for $C_{92}H_{72}N_8O_4Pt$: C, 71.35 H, 4.69; N, 7.24; Pt, 12.60. Found: C, 72.31; H, 4.65; N, 7.75; Pt, 11.94.

TETRAKIS (CUMYLPHENOXY) PHTHALOCYANINE MAGNESIUM (VII)

A mixture of 0.50 g (1.48 mmol) of I and 0.14 g (5.92 mmol) of Mg powder (lightly etched with dilute HCl) was reacted at 280° C. for 70 h: yield 0.072 g (14%); UV-vis (dry dioxane) 282, 380, 615, 680 nm; IR (supported film on NaCl) 3091 w, 3061 w, 3039 w, 2976 m, 2940 w, 2878 w, 1606 s, 1508 s, 1488 s, 1237 s, 1178 m, 1085 m, 1049 m, 952 m, 832 m, 702 s cm$^{-1}$; mass spectrum, m/e 1377 (P+1).

Anal. Calcd for $C_{92}H_{72}N_8O_4Mg$: C, 80.19; H, 5.27; N, 8.13; Mg, 1.76. Found: C, 80.70; H, 5.22; N, 7.48; Mg, 1.42

TETRAKIS (CUMYLPHENOXY) PHTHALOCYANINE COBALT (IX)

A mixture of 0.676 g (2.00 mmol) of I and 0.236 g (4.00 mmol) of Co powder (HCl etched, washed, and dried) was reacted at 280° C. for 12 h: yield 0.249 g (35%); UV-vis (dioxane) 275, 342, 603, 669 nm; Ir (supported film on NaCl) 3093 w, 3063 w, 3041 w, 2987 m, 2941 w, 2879 w, 1608 s, 1509 s, 1476 s, 1413 s, 1242 s, 1182 m, 1137 m, 1102 m, 1063 m, 1020 m, 963 m, 831 m, 767 m, 756 s, 702 s cm$^{-1}$; ESR (1:10 CoPcX$_4$: H$_2$PcX$_4$, toluene, $-90°$ C.) g=2.9 (eight lines); mass spectrum, m/e 1412 (P+1).

Anal. Calcd for $C_{92}H_{72}N_8O_4Co$: C, 78.23; H, 5.14; N, 7.93; Co, 4.17. Found: C. 77.77; H, 5.13; N, 7.92; Co, 4.07

TETRAKIS (CUMYLPHENOXY) PHTHALOCYANINE ZINC (X)

A mixture of 0.676 g (2.00 mmol) of I and 0.262 g (4.00 mmol) of Zn powder (HCl etched, washed, dried) was reacted at 280° C. for 70 h: yield 0.397 g (56%); UV-vis (dioxane) 281, 350, 609, 674 nm; IR (film supported on NaCl) 3039 w, 3063 w, 3040 w, 2988 m, 2940 w, 2879 w, 1607 s, 1508 s, 1493 s, 1476 s, 1402 m, 1361 m, 1240 s, 1179 m, 1122 m, 1092 m, 1050 m, 1021 m, 952 m, 832 m, 767 m, 750 s, 703 s cm$^{-1}$, mass spectrum m/e 1417 (P+1).

Anal. Calcd for $C_{92}H_{72}N_8O_4Zn$: C, 77.87; H, 5.11; N, 7.90; Zn, 4.61. Found: C, 77.86; H, 4.85, N, 7.86; Zn, 4.58.

TETRAKIS (CUMYLPHENOXY) PHTHALOCYANINE LEAD (XI)

A mixture of 0.500 g (1.48 mmol) of I and 0.250 (1.12 mmol) of PbO (fisher, yellow) was reacted at 210° C. for 14 h: yield 0.280 g (49%); UV-vis (dioxane) 244, 270, 339, 360 sh, 383 sh, 638, 710 nm; IR (film supported on NaCl) 3092 w, 3063 w, 3042 w, 2986 m, 2938 w, 2877 w, 1606 s, 1525 m, 1508 s, 1487 s, 1392 m, 1344 m, 1238 s, 1180 m, 1083 m, 1050 m, 950 m, 832 m, 768 m, 750 m, 702 s cm$^{-1}$; mass spectrum, m/e 1561 (P+1).

Anal. Calcd for $C_{92}H_{72}N_8O_4Pb$: C, 70.80; H, 4.65; N, 7.18; Pb, 13.27. Found: C, 70.80; H, 4.65; N, 7.18; Pb, 13.27. Found: C, 70.74; H, 4.89; N, 7.46; Pb, 13.03.

TETRAKIS (CUMYLPHENOXY) PHTHALOCYANINE BISMUTH (XII)

A mixture of 0.676 g (2.00 mmol) of I and 0.84 (4.0 mmol) of Bi powder (HNO$_3$ etched, washed, dried) was reacted at 290° C. for 150 h: yield 0.164 g (21%); UV-vis (dioxane) 287, 343, 663, 696 nm; IR (film supported on NaCl) 3093 w, 3062 w, 3040 w, 2979 m, 2940 w, 2880 w, 1606 s, 1508 s, 1478 s, 1390 m, 1330 m, 1238 s, 1179 m, 1079 m, 1020 m, 947 m, 823 m, 768 m, 743 m, 702 s cm$^{-1}$; mass spectrum, m/e 1562 (P+1).

Anal. Calcd for $C_{92}H_{72}N_8O_4Bi$: C, 70.71; H, 4.64; N, 7.17; Bi, 13.37. Found: C, 72.96; H, 5.06; N, 7.74: Bi, 12.42, 14.22.

TETRATHIOPHENOXY PHTHALOCYANINE (XIII)

A mixture of 0.280 part 4-(phenylthio) phthalonitrile and 0.073 part hydroquinone were reacted at 185° C. for 24 hours. The reaction mixture is dissolved in a minimum of chloroform, chromatographed on alumina with tetrahydrofuran elution, precipitated into methanol, soxhlet extracted with methanol and vacuum dried. The tetrathiophenoxy phthalocyanine is a blue powder.

TETRANEOPENTROXY PHTHALOCYANINE (XIV)

A mixture of 0.59 part 4-neopentoxyphthalonitrile and 0.076 part hydroquinone were reacted at 160° C. for 20 hours. The reaction mixture was dissolved in a minimum of dioxane, chromatographed on alumina, precipitated into methanol and vacuum dried. The tetraneopentoxyphthalocyanine is a purple powder.

TETRA-(OCTADECYL) COPPER PHTHALOCYANINE (XV)

A mixture of 0.50 part 4-octadecyloxy phthalonitrile and 0.16 part copper bronze were reacted at 280° C. for 57 hours. The reaction mixture was dissolved in minimum of toluene, chromatographed on alumina with tetrahydrofuran elution, precipitated into methanol and soxhlet extracted with methanol. Tetra-(octadecyl) copper phthalocyanine is a blue powder which melts above 140° C.

MONOCUMYLPHENOXYPHTHALOCYANINE (XVI)

A mixture of 0.57 part 4-cumylphenoxy-4-phthalonitrile, 2.16 part phthalonitrile and 0.51 part hydroquinone was reacted at 225° C. for 4 hours. The mixture was ground, partially dissolved in tetrahydrofuran and filtered. The filtrate was chromatographed on alumina with tetrahydrofuran elution, precipitated into methanol followed by methanol extraction. This production was analyzed by infrared, UV-vis and mass spectroscopy and found to be dicumylphenoxy phthalocyanine. The monocumylphenoxyphthalocyanine could be soxhlet extracted from the filtered residue with ortho dichlorobenzene.

Obviously, numerous modifications and variations of the above invention are possible in light of the above examples. The examples given are meant to illustrate the teachings of the invention, but not to limit them in any way.

What is claimed and desired to be secured by Letters Patent of the United States is:

1. A device for detecting vapors comprising:
   a substrate;
   electrodes placed upon the substrate; and
   an ordered, semiconductive film, placed such that electricity may flow from one electrode to another through the film;
   wherein the film contains stearyl alcohol as a first component of substituted phthalocyanine in which the substituents are connected to the phthalocyanine ring with ether linkages; and wherein the film further contains a second component which promotes the formation of Langmuir-Blodgett films.

2. The device of claim 1 wherein the phthalocyanine of the said first component contains a selected central metal atom, which metal atom is selected from the group consisting of Ni, Co, Pb, Fe, Pd, Pt, and Zn.

3. The device of claim 2 wherein the said first component of the film is tetracymylphenoxy phthalocyanine with the said selected metal atom, and the said second component of the film is stearyl alcohol.

4. The device of claim 3 wherein said first component and said second component are present in substantially equimolar amounts.

5. A device for detecting vapors comprising:
a substrate composed of quartz;
interdigital electrodes placed upon the substrate; and
an ordered, semiconductive film, placed such that electricity may flow from one electrode to another through the film;
wherein the film contains a first component of metal-containing tetracymylphenoxy phthalocyanine in which the metal is selected from the group consisting of Ni, Co, Pb, Fe, Pd, Pt, and Zn; and
wherein the film further contains a second component consisting of stearyl alcohol.

6. A device for detecting vapors comprising:
a substrate composed of quartz;
interdigital electrodes placed upon the substrate; and
an ordered, semiconductive film, placed such that electricity may flow from one electrode to another through the film;
wherein the film contains a first component of tetracymylphenoxy phthalocyanine which contains two hydrogen atoms in place of a metal atom at the center of the phthalocyanine ring; and
wherein the film further contains a second component consisting of stearyl alcohol.

7. The device of claim 1 wherein the phthalocyanine of the said first component contains two hydrogen atoms at the center of phthalocyanine ring, which hydrogen atoms occupy the site which could otherwise be occupied by a metal atom.

* * * * *